(12) United States Patent
Park et al.

(10) Patent No.: US 10,543,120 B2
(45) Date of Patent: Jan. 28, 2020

(54) BELT ADDITIONAL SUBSTANCE HAVING SELF-HEATING AND FUNCTIONALITY USING GRAPHENE AND NANO INORGANIC SUBSTANCE, AND BELT AND MANUFACTURING METHOD USING THE SAME

(71) Applicants: Sang Hoon Park, Daejeon (KR); Lee Hak Jung, Daejeon (KR)

(72) Inventors: Sang Hoon Park, Daejeon (KR); Lee Hak Jung, Daejeon (KR)

(*) Notice: Subject to any disclaimer, the term of this patent is extended or adjusted under 35 U.S.C. 154(b) by 527 days.

(21) Appl. No.: 15/366,294

(22) Filed: Dec. 1, 2016

(65) Prior Publication Data

US 2017/0172789 A1    Jun. 22, 2017

(30) Foreign Application Priority Data

Dec. 22, 2015  (KR) .................. 10-2015-0183614

(51) Int. Cl.
*A61F 7/02*     (2006.01)
*A41D 20/00*    (2006.01)
(Continued)

(52) U.S. Cl.
CPC .............. *A61F 7/02* (2013.01); *A41D 20/00* (2013.01); *B29C 35/045* (2013.01);
(Continued)

(58) Field of Classification Search
CPC .......................... A61M 11/041; A61M 11/047; A61M 11/048; A61M 15/0003; A61M 35/00; A61M 31/00; A61F 7/02; A61F 2007/0231; A61F 2007/0098; A61F 2007/0234; A61F 2007/0088; A61F 2007/0228; A61F 2007/0266; A41D 20/00; A41D 2400/10; A41D 2400/32; A41D 2500/50; B29C 35/045; B29C 44/341; B29C 44/02;
(Continued)

(56) References Cited

U.S. PATENT DOCUMENTS

2010/0065052 A1* 3/2010 Sharma ................ A61M 11/041
                                                                   128/204.17
2016/0223269 A1* 8/2016 Hartmann ........... H01L 23/4275

FOREIGN PATENT DOCUMENTS

KR    20-0329046 Y1    10/2003
KR    10-1436095 B1     9/2014
(Continued)

*Primary Examiner* — Robert C Dye
*Assistant Examiner* — Taryn Trace Willett
(74) *Attorney, Agent, or Firm* — Paratus Law Group, PLLC

(57) ABSTRACT

A method for manufacturing a belt, which molds a heating member 13 by 20 to 98 parts by weight selecting at least one of nonferrous metals constituted by tourmaline, bentonite, pozzolan, mica, red clay, zeolite, magnesium oxide, white clay, calcium, and silica, 0.1 to 30 parts by weight selecting at least one of A type Tio sol, Ag sol, and Zno having a particle size of 5 to 20 nm, graphene 01 to 10 parts by weight having a particle size of 0.20 to 2.25 nm, and functional metal colloidal 0.05 to 8 parts by weight having a size of 1 to 10 nm by selecting at least one of Ag, Au, Zn Pt, and Y, 20 to 98 parts by weight are combined by selecting at least one of the nonferrous metals and thereafter, ground into particle sizes of 500 to 1500 meshes.

11 Claims, 3 Drawing Sheets

(51) Int. Cl.
    *B29C 35/04*     (2006.01)
    *B29C 44/34*     (2006.01)
    *A61F 7/00*     (2006.01)
    *B29K 105/24*     (2006.01)
    *B29C 44/02*     (2006.01)
    *B29K 27/06*     (2006.01)
    *B29K 83/00*     (2006.01)
    *B29K 105/16*     (2006.01)
    *B29K 507/04*     (2006.01)
    *B29K 509/00*     (2006.01)
    *B29L 31/48*     (2006.01)
    *B29L 31/00*     (2006.01)

(52) U.S. Cl.
    CPC ...... B29C 44/3415 (2013.01); *A41D 2400/10* (2013.01); *A41D 2400/32* (2013.01); *A41D 2500/50* (2013.01); *A61F 2007/0088* (2013.01); *A61F 2007/0098* (2013.01); *A61F 2007/0228* (2013.01); *A61F 2007/0231* (2013.01); *A61F 2007/0234* (2013.01); *A61F 2007/0266* (2013.01); *B29C 44/02* (2013.01); *B29K 2027/06* (2013.01); *B29K 2083/005* (2013.01); *B29K 2105/162* (2013.01); *B29K 2105/24* (2013.01); *B29K 2507/04* (2013.01); *B29K 2509/00* (2013.01); *B29K 2995/0012* (2013.01); *B29L 2031/48* (2013.01); *B29L 2031/753* (2013.01)

(58) Field of Classification Search
    CPC .......... B29K 2105/24; B29K 2105/162; B29K 2027/06; B29K 2083/005; B29K 2507/04; B29K 2509/00; B29K 2995/0012; B29L 2031/753; B29L 2031/48
    See application file for complete search history.

(56) References Cited

FOREIGN PATENT DOCUMENTS

| KR | 101436095 B1 * | 9/2014 |
|---|---|---|
| KR | 10-2015-0079419 A | 7/2015 |
| KR | 10-1540439 B1 | 7/2015 |

\* cited by examiner

BELT ADDITIONAL SUBSTANCE HAVING SELF-HEATING AND FUNCTIONALITY USING GRAPHENE AND NANO INORGANIC SUBSTANCE, AND BELT AND MANUFACTURING METHOD USING THE SAME

CROSS REFERENCE TO PRIOR APPLICATION

This application claims priority to Korean Patent Application No. 10-2015-0183614, filed on Dec. 22, 2015, which is hereby incorporated by reference in its entirety.

BACKGROUND

The present invention relates to a belt additional substance having self-heating and functionality using graphene and a nano inorganic substance, and a belt and a manufacturing method using the same, and more particularly, to a belt additional substance having self-heating and functionality using graphene and a nano inorganic substance, in which energy of heat radiated from a body temperature energy is transferred to heating elements attached to a belt without using energy from the outside to increase the heat by a mechanism of radiation, rise, and heating, and as a result, multi-functions of the belt give various benefits to a human body, and a belt and a manufacturing method using the same.

In general, a waist belt is called a waist support or a waist band and in general, has a large width by using a material such as spandex and the waist belt is worn on a waist by sealing a buckle or a nylon made bonded fabric (Velcro magic tape) on the front end of the waist belt and the waist belt widely supports the waist while slightly pressing the waist to make the waist be convenient while the waist is squared, thereby protect the waist without a pain.

In recent years, a waist belt having a structure in which a heat wire is embedded has appeared in order to provide thermal stimulation and therapy effects to a waist portion or an abdomen portion together with the effect of the waist belt, but the waist belt has a lot of problems including a complicated structure, increased power consumption, harmful electromagnetic waves generated in a human body when the waist belt is used, and the like. Therefore, provided is a waist belt in which a pocket is formed in the waist belt and a fomentation pack is accommodated in the pocket without using electricity so as to acquire the thermal stimulation effect.

However, in the case of the waist belt accommodating the fomentation pack, since the fomentation packet is warmed by using the energy, this is also very difficult and the resulting energy consumption cannot be avoided and since the fomentation pack is gradually cooled with the elapse of a used time, a fomentation effect cannot be continued.

Therefore, in Korean Patent Registration No. 1540439 (registered on Aug. 25, 2014), a tourmaline ball formed in an inner skin contacts a skin and a sheet laminated with graphene is positioned between an outer skin and the inner skin to increase heating efficiency.

However, tourmaline emits heat by using the graphene and the heat deeply permeates into the skin to shorten a heat emission time, but a radiation mechanism of far infrared rays cannot be effectively used, and as a result, various effects which can be provided cannot be normally maintained.

PRIOR ART DOCUMENT

Patent Document (Patent Document 0001) Document 1. Korean Patent Registration No. 1436095 (registered on Aug. 25, 2014)

(Patent Document 0002) Document 2. Korean Patent Registration No. 1540439 (registered on Jul. 23, 2015)

(Patent Document 0003) Document 3. Korean Patent Laid-open Publication No. 2015-0079419 (registered on Jul. 8, 2015)

(Patent Document 0004) Document 4. Korean Utility Model Registration No. 0329046 (registered on Sep. 25, 2003)

SUMMARY

Accordingly, the present invention is contrived to solve the problems in the related art and an object of the present invention is to provide a heating belt which radiates heat radiated from a body temperature and increases the radiated heat by a heating action to be reheated.

Another object of the present invention is to provide various functionalities as photovoltaic heat, body temperature heat, other heat sources, and the like as heat sources by using a nano inorganic material is increased and heated as heat radiant energy to discharge heat or be transferred to a subcutaneous deep layer in a skin.

Yet another object of the present invention is to synthesize environmentally friendly organic polymers and inorganic polymers to have tension and flexible performance to be variously applied like a human body attachment type, a belt, and an abdomen band type.

Still yet another object of the present invention is to effectively reach and form a wavelength band of a human body in a far infrared-ray radiation mechanism to lighten a body and provide an anti-bacterial activity, and deodorization and air purification functions.

In a method for manufacturing a belt using a belt additional material having self-heating and functionality using graphene and a nano inorganic material, which molds a heating member 13 by 20 to 98 parts by weight selecting at least one of nonferrous metals constituted by tourmaline, bentonite, pozzolan, mica, red clay, zeolite, magnesium oxide, white clay, calcium, and silica, 0.1 to 30 parts by weight selecting at least one of A type Tio sol, Ag sol, and Zno having a particle size of 5 to 20 nm, graphene 01 to 10 parts by weight having a particle size of 0.20 to 2.25 nm, and functional metal colloidal 0.05 to 8 parts by weight having a size of 1 to 10 nm by selecting at least one of Ag, Au, Zn Pt, and Y, 20 to 98 parts by weight are combined by selecting at least one of the nonferrous metals and thereafter, ground into particle sizes of 500 to 1500 meshes.

According to the present invention, provided is a heating belt that provides various benefits to a human body through multi-functions by increasing heat in a radiation—increase—heating mechanism in which heat radiated from a body temperature is radiated by a belt and the radiated heat is increased and re-emitted through a heat generation operation.

According to the present invention, provided are various functional effects in which only the existing heat sources are applied by using a nano inorganic material and photovoltaic heat, body temperature heat, other heat sources, and the like become heat sources to be increased and emitted as radiation heat energy and thereafter, the heat is discharged and transferred up to a subcutaneous deep layer in a skin and a capillary is expanded to promote blood circulation or a clogged vessel is bored and a pain of a sick portion is alleviated.

According to the present invention, tension and flexible performance are acquired through organic and inorganic synthesis and fixation that synthesizes environmentally friendly organic polymers and inorganic polymers, and as a result, a belt is variously applied like a human body attachment type, a belt, and a waist support to be used in various portions of the human body.

According to the present invention, a wavelength band is formed, which effectively reaches a 9.36-micron wavelength band of the human body in a far infrared radiation mechanism, and as a result, a resonance action, a rotary motion, an expansion motion, a translation motion, and an angle variation motion are forcibly performed intensively at a phenomenal speed of $Sec/10^{-12}$ to lighten a body and the capillary is expanded to promote blood circulation and an inorganic antimicrobial agent which is harmless to the human body gives an antibacterial activity to protect the human body from human body harmful strains generated at a wearing portion and a deodorization function is expressed to suppress a smell of sweat and purify air from various types of smells.

DETAILED DESCRIPTION

Figure 1:
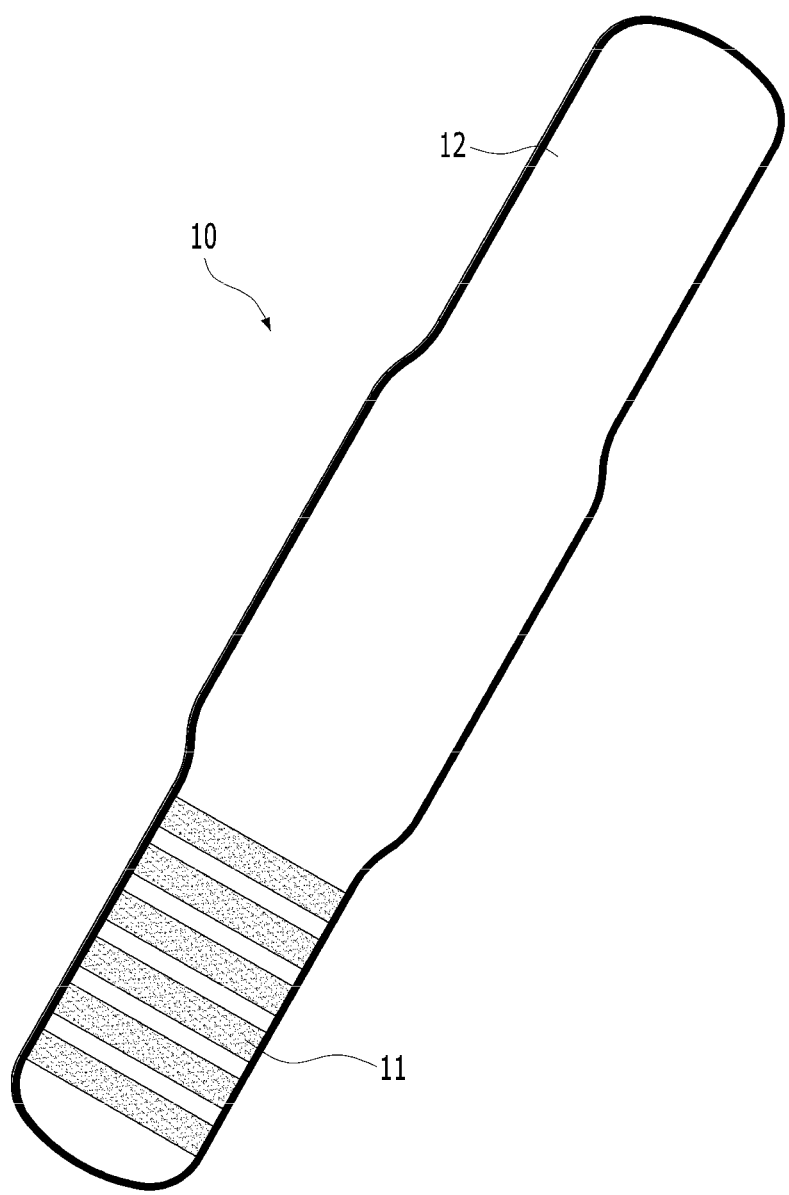
FIG. 1 is a surface diagram of a belt according to a preferred embodiment of the present invention.

Hereinafter, preferred embodiments of the present invention will be described in more detail with reference to the accompanying drawings.

The present invention consists of 20 to 98 parts by weight selecting at least one of nonferrous metals constituted by tourmaline, bentonite, pozzolan, mica, red clay, zeolite, magnesium oxide, white clay, calcium, and silica, 0.1 to 30 parts by weight selecting at least one of A type Tio sol, Ag sol, and Zno having a particle size of 5 to 20 nm, graphene 01 to 10 parts by weight having a particle size of 0.20 to 2.25 nm, and functional metal colloidal 0.05 to 8 parts by weight having a size of 1 to 10 nm by selecting at least one of Ag, Au, Zn Pt, and Y.

The mixture is formed to be shown on the surface of rubber by any one method of coating and printing, and serves as a support on the surface of the rubber and radiates far infrared rays.

20 to 98 parts by weight are combined by selecting at least one of the nonferrous metals constituted by the tourmaline, bentonite, pozzolan, mica, red clay, zeolite, magnesium oxide, white clay, calcium, and silica and thereafter, ground into particle sizes of 500 to 1500 meshes.

The ground nonferrous metal is formed by any one method of the coating and the printing and when the ground nonferrous metal is equal to or less than 500 meshes, the sizes of the particles are too large, and as a result, fixation and far infrared-way radiation actions are difficult and when the ground nonferrous metal has a particle size of 1500 meshes or more, cost for grinding is large and the far infrared-ray radiation action does not increase, and as a result, nonferrous metal is preferably ground into 1000 meshes.

Powder 100 w % ground into the particle size of 500 to 1500 meshes is mixed and agitated with pure water (distilled water) 300 w % in an agitator container.

An ion binder Na-EDTA of 0.01 to 10 w % is added to a mixture of the ground powder and the pure water of 100 w % and thereafter, is made into suspension.

The ion binder serves to fix ionization to improve mutual binding force.

In a process that selects at least one of A type Tio sol, Ag sol, and ZnO having the particle size of 5 to 20 nm to be made into the suspension, the belt is manufactured by slowly inputting 0.1 to 30 parts by weight into the agitator so as to facilitate ion substitution in each particle.

In the case of a container temperature of the agitator, ion substitution is performed by maintaining a temperature of 40 to 60 C for 4 to 6 hours.

In maintaining the container temperature of the agitator at 40° C. or less, molecule substitution is not smooth and maintaining the temperature at 60° C. or more degrades, and as a result, preferably, the binding force of molecules is enhanced by maintaining the temperature at 50° C. for 5 hours to fix the molecules to each other.

The graphene is provided, which has purity of 99.9% or more and a particle size of 0.20 to 0.25 nm and 0.1 to 10 parts by weight is slowly added.

Electrons of the graphene as a conjugate of a natural carbon material and a high molecular compound are composite nano materials having an electron movement speed of 9 million km per sec which is 3 hundred times higher than the speed of light, stores thermal energy and light energy of carbon, and emit negative ions and the far infrared rays, and the graphene as a material having an energy storage material characteristic, that is, capable of thermal and light energy is a thermal conductive new material.

At least one of Ag, Au, Zn, Pt, and Y is selected and selected as a chelate agent having the particle size of 1 to 10 nm and the selected material 0.05 to 8 parts by weight is slowly added through the ion substitution.

The chelate is added to the selected material through the ion substitution and sufficiently agitated slurry is input into a heat wind dryer at 150 to 200° C. and thereafter, dried for 5 to 6 hours.

The heat wind dryer is easy to perform mineral dry to enable rapid and uniform dry of even the inside, thereby sufficiently drying slurry with a heat wind.

The slurry is dried and thereafter, input into a grinder again and particles are reduced to a high powder state (1 to 10 nm).

In the case of the high powder state acquired through the reduction, 10 to 100 parts by weight is input into 100 parts by weight of any one resin of silicon rubber and PVC rubber and thereafter, agitated at a speed of 50 to 100 rpm for 10 to 20 minutes to be made into the slurry.

Since the high-powder state is an emulsion type, the high-powder state is made into paste-state slurry by agitation.

The slurry state material is molded and injected so as to have any one of a quadrangle, a triangle, a circle, a logo, and a pattern to be attached to a fiber surface through the injected and molded heating member 13.

After the slurry state material is attached to the fiber surface, the slurry state material attached to the fiber surface passes through the heat wind dryer maintaining the temperature of 100 to 250° C. for 10 to 20 minutes to be thermally cured.

In the heat wind dryer, when nitrogen or hydrogen is deformed in the rubber, a form and a shape are maintained and a foaming agent of 0.001 to 1 w % is input into a total material of 100 w % to be thermally cured.

Figure 2:
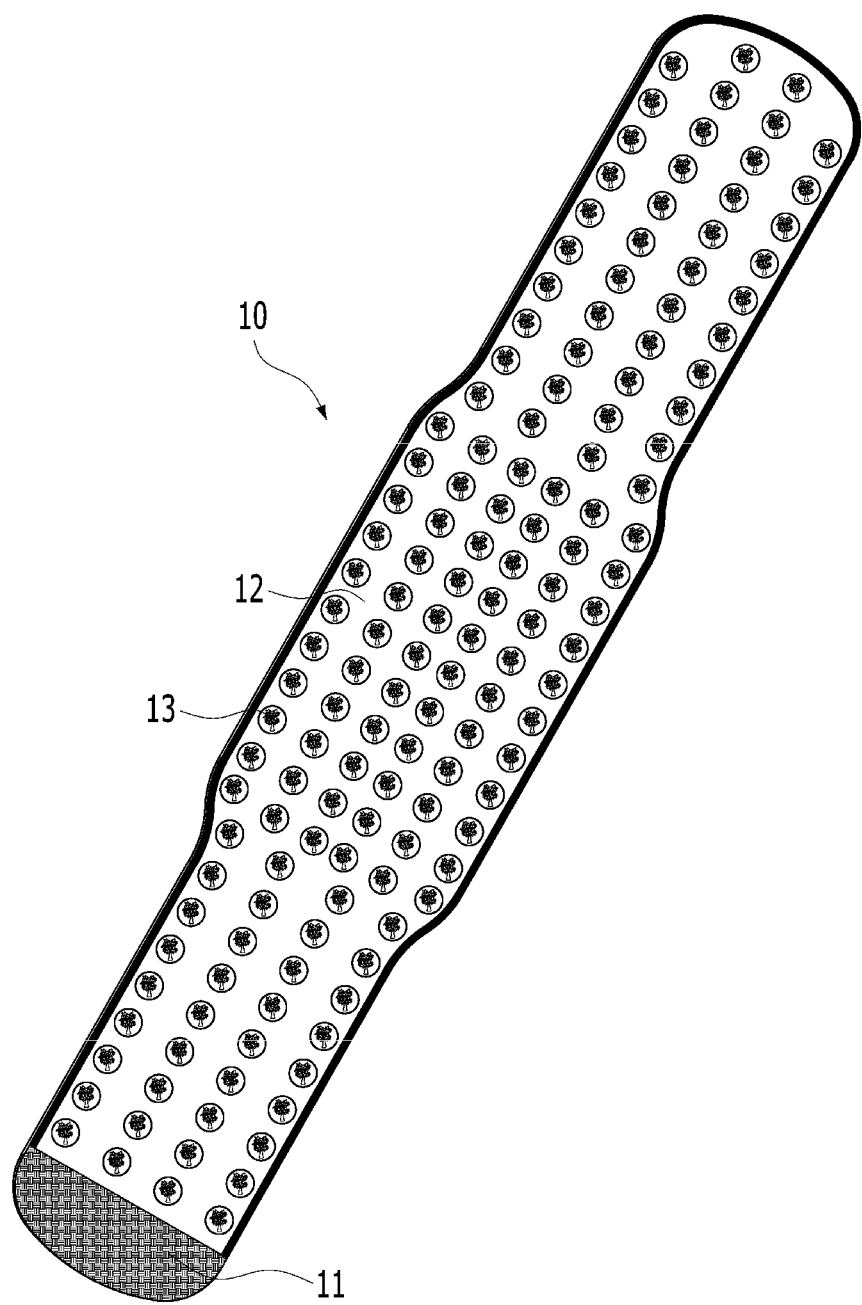
FIG. 2 is an inner surface diagram of a belt according to a preferred embodiment of the present invention.
Figure 3:
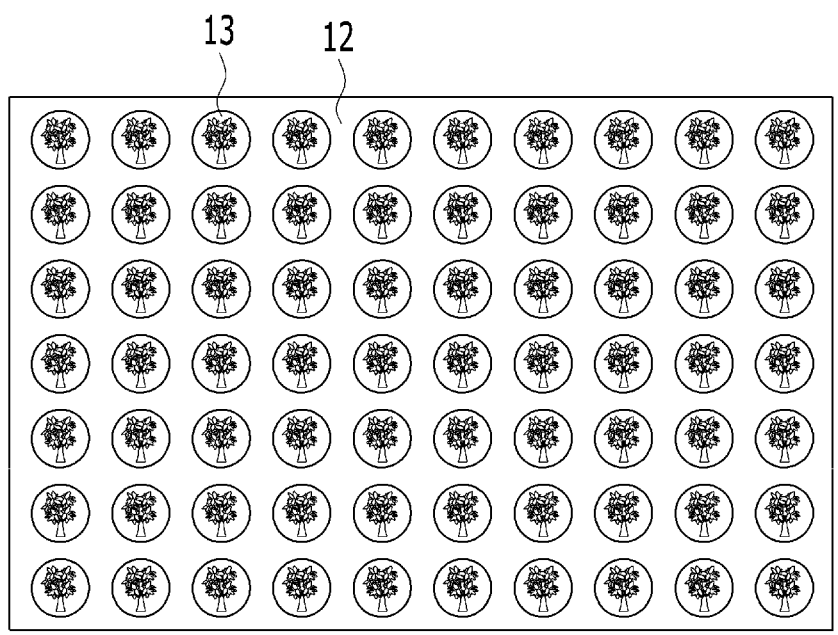
FIG. 3 is an inner surface diagram of a primary part for the belt according to the present invention.

The belt 10 made of the material as illustrated in FIGS. 1 to 3 is worn in parts of the human body, such as a waist, an arm, a shoulder, a knee, an ankle, a wrist, and the like and multiple magic tapes 11 are installed on one side of an outer surface at a predetermined interval and a fiber 12 is provided to a part contacting the human body through wearing in an opposite direction and thereafter, a heating member 13 is installed by any one method of printing, coating, molding, and fixing a material on the surface of the fiber 12.

The belt 10 is worn so that the heating member 13 contacts any one part of the human body and when the belt 10 is worn, heat is radiated from a body temperature of the body and energy is transferred to the heating members 13, and as a result, the temperature of the body increases up to a maximum of 3° C. after 20 to 30 minutes depending on a person by a mechanism of radiation—increase—heating action.

The heating member 13 does not receive a heat source from the outside and photovoltaic heat, body temperature heat, other heat resources, and the like become heat sources and increased and emitted as radiation heat energy and thereafter, the heat is discharged to be transferred up to a subcutaneous deep layer in a skin and a capillary is expanded to promote blood circulation and a clogged blood vessel and a pain of a sick portion is alleviated.

That is, through a far infrared-ray radiation mechanism in which four motions of translation, angle variation, rotation, and expansion are performed at a phenomenal speed of $10^{-12}$ (1 trillion) per second to given a resonance phenomenon, various efficacy is provided.

In the heating member 13, an inorganic antimicrobial agent which is harmless to the human body gives an antibacterial activity shows a semi-permanent an antibacterial activity to prevent urtication of the skin and damage of the skin with a material which is resistant to the antibacterial activity, such as *Staphylococcus aureus, Diplococcus pneumoniae, Pseudomonas aeruginosa*, mold spores, and the like which live while being attached to the skin generated at a wearing portion and provides an deodorization function to suppress a small of sweat and provide an effect of air purification.

According to the present invention, provided is a very useful invention in which heat radiated from a body temperature is radiated in a heating member of a belt and temperature increases and is transferred to a skin through re-heating to give a heating effect of a whole body, thereby providing various effects through hyperthermia, mature, magnetism, dryness and wetness, neutralization, and resonance actions.

What is claimed is:

1. A method for manufacturing a belt using a belt additional material having self-heating and functionality using graphene and a nano inorganic material, the method comprising:
    molding a heating member including:
        20 to 98 parts by weight of nonferrous metals including at least one of tourmaline, bentonite, pozzolan, mica, red clay, zeolite; magnesium oxide, white clay, calcium; and silica,
        0.1 to 30 parts by weight of at least one material, including at least one of A type Tio sol, Ag sol, and Zno, having a particle size of 5 to 20 nm,
        01 to 10 parts by weight of graphene having a particle size of 0.20 to 2.25 nm, and
        0.05 to 8 parts by weight of functional metal colloidal, having a particle size of 1 to 10 nm, including at least one of Ag, Au, Zn, Pt, and Y; and
    fixing the heating member on a surface of the belt,
    wherein the molding includes:
        grinding the 20 to 98 parts by weight of the nonferrous metals to have particle sizes of 500 to 1500 meshes,
        mixing ground nonferrous metals with water at a 1:3 weight ratio of the ground nonferrous metals to the water, and
        agitating a mixture of the ground nonferrous metals and the water in an agitator container.

2. The method of claim 1, wherein the molding further includes adding an ion binder Na-EDTA to the mixture at a 0.01-10:100 weight ratio of the ion binder Na-EDTA to the water during the agitating to make the mixture into suspension.

3. The method of claim 2, wherein the molding further includes adding the 0.1 to 30 part by weight of the at least one material, including the at least one of A type Tio sol, Ag sol, and ZnO, having the particle size of 5 to 20 nm into the agitator container while making the mixture into the suspension.

4. The method of claim 3, wherein the molding further includes maintaining a temperature of 40 to 60° C. for 4 to 6 hours in the agitator container during the agitating.

5. The method of claim 2, wherein the molding further includes adding, the 0.05 to 8 parts by weight of the functional metal colloidal, having the particle size of 1 to 10 nm, including the at least one of Ag, Au, Zn, Pt, and Y, selected as a chelate agent into the suspension during the agitating to make the suspension into agitated slurry.

6. The method of claim 5, wherein the molding further includes drying the agitated slurry using a heat wind dryer at 150 to 200° C. for 5 to 6 hours.

7. The method of claim 6, wherein the molding further includes grinding dried slurry using a grinder into powder having particle sizes in a range of 1 to 10 nm.

8. The method of claim 7, wherein the molding further includes mixing the powder with any one resin of silicon rubber and PVC rubber at a 0.1-1:1 weight ratio of the powder to the any one resin of the silicon rubber and the PVC rubber, and agitating mixed powder and the any one resin of the silicon rubber and the PVC rubber at a speed of 50 to 100 rpm for 10 to 20 minutes to make slurry.

9. The method of claim 8, wherein the molding further includes shaping the heating member in a quadrangle, a triangle, a circle, a logo, or a pattern, and
    wherein the fixing includes attaching shaped heating member to the surface of the belt.

10. The method of claim 9, wherein the fixing further includes thermally curing the shaped heating member attached to the surface of the belt using the heat wind dryer at a temperature of 100 to 250° C. for 10 to 20 minutes.

11. The method of claim 10, wherein the thermally curing includes applying a foaming agent on the surface of the belt.

* * * * *